United States Patent
Duling et al.

(10) Patent No.: US 7,161,686 B2
(45) Date of Patent: Jan. 9, 2007

(54) SENSOR FOR DETERMINING THE ANGULAR POSITION OF A RADIATING POINT SOURCE IN TWO DIMENSIONS AND METHOD OF OPERATION

(75) Inventors: Alec Duling, Milton, VT (US); Don Odell, Milton, VT (US)

(73) Assignee: Ascension Technology Corporation, Burlington, VT (US)

(*) Notice: Subject to any disclaimer, the term of this patent is extended or adjusted under 35 U.S.C. 154(b) by 252 days.

(21) Appl. No.: 10/705,853

(22) Filed: Nov. 13, 2003

(65) Prior Publication Data

US 2005/0105101 A1    May 19, 2005

(51) Int. Cl.
G01B 11/14 (2006.01)
G01C 21/02 (2006.01)

(52) U.S. Cl. ............... 356/614; 356/141.5; 250/206.1; 250/206.2; 250/216

(58) Field of Classification Search ........ 356/614–625, 356/638, 604, 610, 141.5, 141.2; 250/206.2, 250/206.1, 203.4, 203 R, 216, 237 R, 204.4
See application file for complete search history.

(56) References Cited

U.S. PATENT DOCUMENTS

| | | | | |
|---|---|---|---|---|
| 4,092,072 A | * | 5/1978 | Ellis | 356/141.5 |
| 4,314,761 A | * | 2/1982 | Reymond et al. | 356/141.5 |
| 4,794,245 A | * | 12/1988 | Auer | 250/206.2 |
| 4,810,870 A | * | 3/1989 | Tsuno et al. | 250/206.1 |
| 4,857,721 A | * | 8/1989 | Dunavan et al. | 250/206.1 |
| 4,874,937 A | * | 10/1989 | Okamoto | 250/206.2 |
| 4,999,483 A | * | 3/1991 | Okamoto | 250/203.1 |
| 5,483,060 A | * | 1/1996 | Sugiura et al. | 250/237 R |
| 5,499,098 A | * | 3/1996 | Ogawa | 356/621 |
| 5,757,478 A | * | 5/1998 | Ma | 356/141.2 |
| 6,274,862 B1 | * | 8/2001 | Rieger | 250/216 |

* cited by examiner

Primary Examiner—Gregory J. Toatley, Jr.
Assistant Examiner—Sang H. Nguyen
(74) Attorney, Agent, or Firm—H. Jay Spiegel

(57) ABSTRACT

A sensor for determining the angular position of a radiating point source in two dimensions includes a mask encoded in two skewed directions with waveforms consisting of several frequencies in prescribed patterns. The frequency spectra of the received detector patterns are computed. In order to facilitate such computations, the constituent frequencies are separated so as to be distinguished in the Fast Fourier Transform (FFT). Each of the frequency patterns that are coded on the variable transmissivity mask consists of a series of low frequencies followed by a series of variable frequencies, and a series of high frequencies. The variable frequencies exhibit frequency changes responsive to various image positions. The low and high frequencies are responsive in phase to variations in image position. The frequency variations in the variable frequencies are used to indicate coarse position while the phases of the fixed low and high frequencies are used to indicate medium and fine position. In a second embodiment, the mask pattern is formed by a first pattern including low variable and high frequency components, a second pattern with fixed low and high frequency components, and a third pattern with variable frequency components. The method of determining position is also disclosed.

20 Claims, 6 Drawing Sheets

Embodiment Using Orthogonal Variable Frequency Components

SENSOR FOR DETERMINING THE ANGULAR POSITION OF A RADIATING POINT SOURCE IN TWO DIMENSIONS AND METHOD OF OPERATION

BACKGROUND OF THE INVENTION

The present invention relates to a sensor for determining the angular position of a radiating point source in two dimensions and its method of operation. The present invention has particular pertinence in the field of surgery, with particular reference to close range surgical instrument tracking. Additionally, the present invention is applicable in the fields of virtual reality and pilot head tracking systems.

In the prior art, systems have been devised that employ one dimensional masked or coded apertures placed above multi-element one dimensional detectors. Such structure is disclosed in U.S. Pat. Nos. 4,810,870 and 5,408,323. In such systems, correlation techniques are employed to determine the position of a projected pseudo-random pattern on a detector surface by comparing signals from fixed detector elements arranged in a unique pattern or from comparison with fixed reference signals previously stored in a computer.

Additionally, it is known in the prior art to use a two dimensional aperture and a one dimensional detector in the form of a charge coupled device (CCD) to determine angular position in two dimensions. Such a system is disclosed in U.S. Pat. No. 4,092,072. A drawback of such a system is that it does not provide immunity from errors resulting from reflections, and does not yield sufficiently high enough resolution as is the case with techniques employing pseudo-random patterns and correlation techniques.

The prior art systems described above, while capable of determining angle of incidence with high resolution, yield only one-dimensional information. The present invention differs from the teachings of these patents as providing high resolution two-dimensional information. It is with this difference in mind that the present invention was developed.

SUMMARY OF THE INVENTION

The present invention relates to a sensor for determining the angular position of a radiating point source in two dimensions and its method of operation. The present invention includes the following interrelated objects, aspects and features:

(1) In a first aspect of the present invention, the present invention includes a method for determining the angular position in two dimensions of a point source of radiation with respect to a detector by examining shifts of periodic components, in two dimensions, of a projected image of a variable transmissivity mask. In the preferred embodiment of the present invention, the mask is encoded in two skewed directions with waveforms consisting of several frequencies in prescribed patterns.

(2) The frequency spectra of the received detector patterns are computed. In order to facilitate such computations, the constituent frequencies are substantially separated so as to be distinguished in the Fast Fourier Transform (FFT).

(3) Each of the frequency patterns that are coded on the variable transmissivity mask consists of a series of low frequencies followed by a series of variable frequencies, and a series of high frequencies. Applicants have found that accurate measurements may be obtained through creation of FFT plots for various pattern shifts. The middle variable frequencies exhibit frequency changes responsive to various image positions. The low and high frequencies that straddle the variable frequencies have been found to be responsive in phase to variations in image position.

(4) Applicants have found that the frequency variations in the variable frequencies may be used to indicate coarse position in each coordinate axis while the phases of the fixed low and high frequencies may be used to indicate medium and fine position in each coordinate axis.

As such, it is a first object of the present invention to provide a sensor for determining the angular position of a radiation point source in two dimensions and the method thereof.

It is a further object of the present invention to provide such a sensor in which a variable transmissivity mask is created by encoding the mask with sequences of frequencies in two skewed or orthogonal directions.

It is a still further object of the present invention to provide such frequency patterns including use of low frequencies followed by variable frequencies followed by high frequencies.

It is a still further object of the present invention to provide such a sensor in which coarse measurements of position may be carried out through measurements of frequency changes in the variable frequencies and medium and fine position measurements may be carried out through variations in the phases of the low and high frequencies.

It is a yet further object of the present invention to provide such a sensor, in a second embodiment thereof, wherein the mask pattern is formed by a first function including low, variable and high frequency components, a second function with fixed low and high frequency components, and a third function with variable frequency components.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
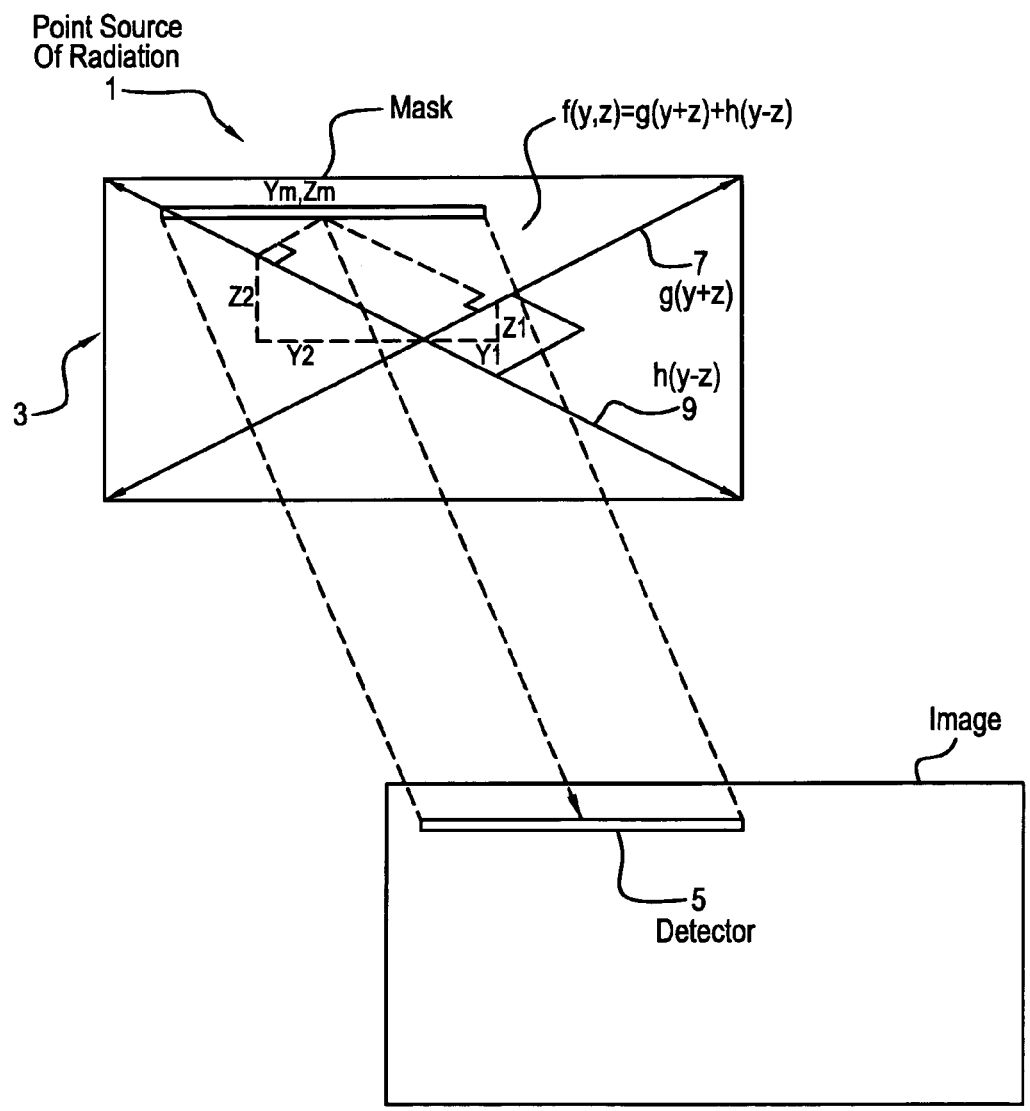
FIG. 1 shows a schematic representation of a preferred embodiment of the present invention.

Reference is first made to FIG. 1 which shows a schematic representation of a first embodiment of the present invention. In FIG. 1, a point source of radiation 1 is directed toward a mask 3. The radiation travels through the mask 3 and, as modified by the mask 3, is received by the detector 5.

With further reference to FIG. 1, the mask 3 has a pattern thereon which is created by a first set of frequencies along the double-headed arrow 7 and a second set of frequencies along the double-headed arrow 9.

Figure 2:
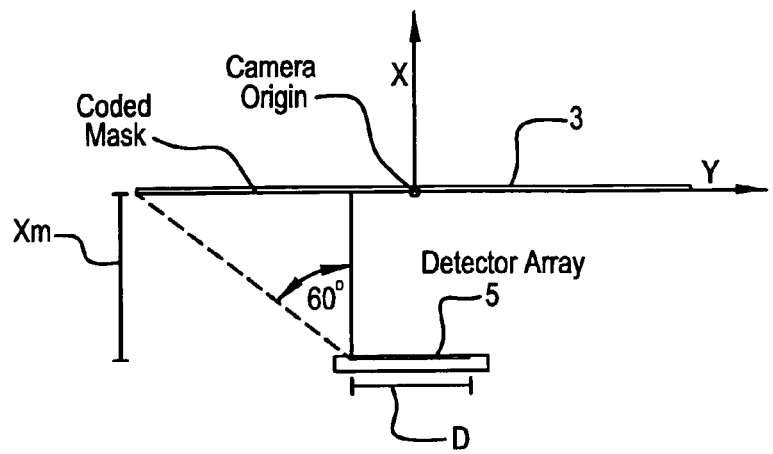
FIG. 2 shows a front view of the embodiment of FIG. 1 showing the X and Y axes.
Figure 3:
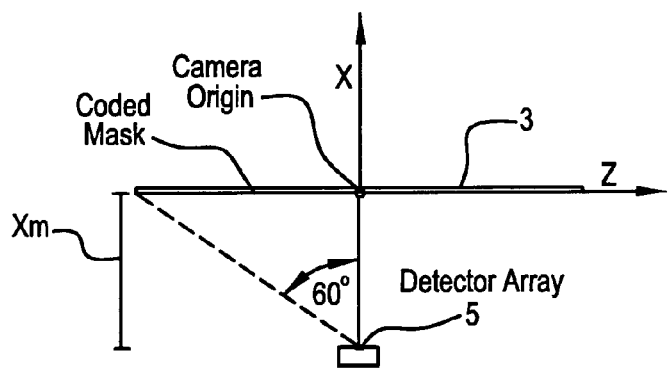
FIG. 3 shows a view rotated 90 degrees from the view of FIG. 2 to show the X and Z axes.
Figure 4:
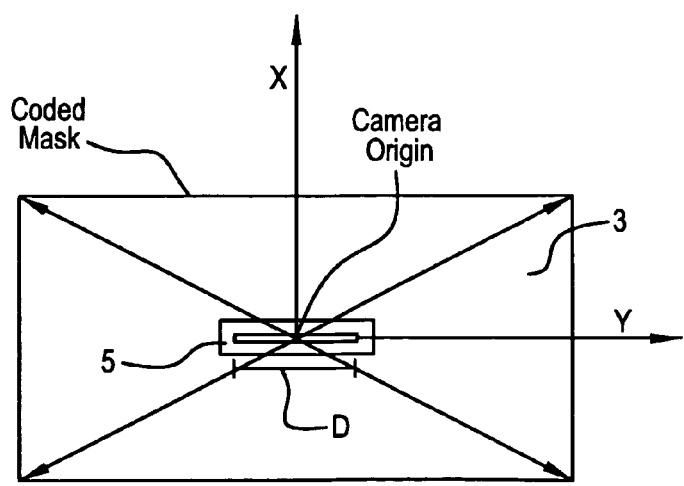
FIG. 4 shows a top view of the embodiment of FIG. 1.
Figure 5:
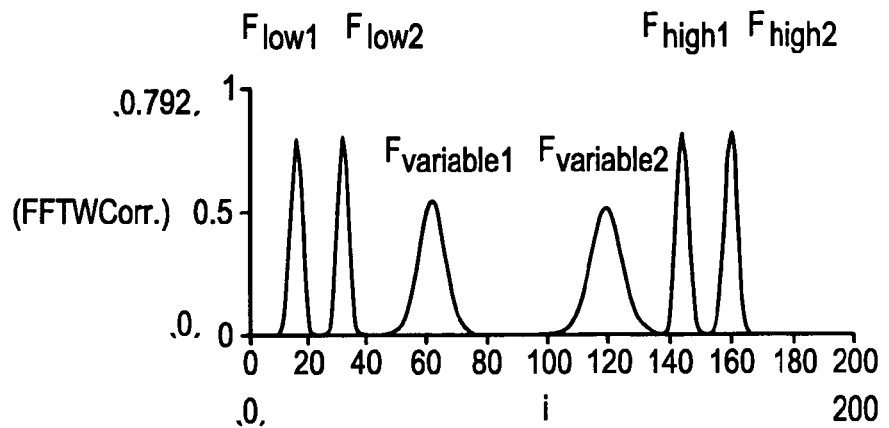
FIGS. 5, 6 and 7 show graphs of computed Fast Fourier Transforms (FFTs) for first, second and third pattern shifts, respectively.
Figure 6:
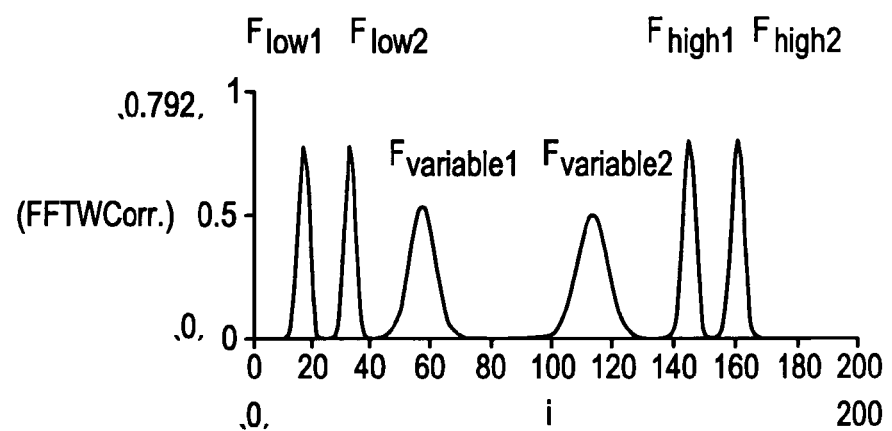
Figure 7:
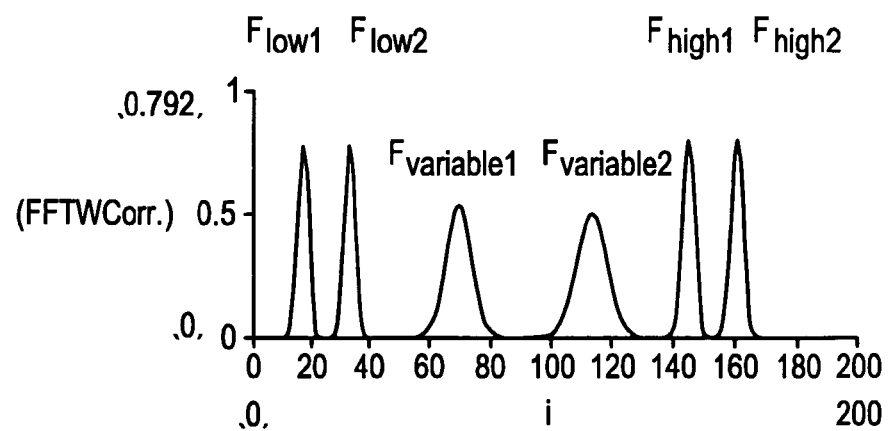

FIGS. 2, 3 and 4 show front, side and top views, respectively, of the system illustrated in FIG. 1. FIGS. 5, 6 and 7 provide a better understanding of the frequency sequences shown at the reference numerals 7 and 9. Each of the frequency sequences consist of at least two low fixed frequencies followed by at least two variable frequencies followed by at least two fixed high frequencies.

The detector 5 may, if desired, consist of a linear CCD detector with the mask 3 situated at a prescribed fixed distance therefrom and, as seen in FIGS. 2 and 3, the mask 3 is preferably in a plane parallel to the plane of the CCD detector array 5. As should be understood from FIGS. 1–4, the point source emitter 1 illuminates the mask 3 casting an image onto the plane of the detector 5. The detected image is recorded in a computer (not shown) and the Fast Fourier Transform (FFT) is computed.

Applicants have found that variations in the frequencies of the variable frequencies shown in the middle of the graphs of FIGS. 5, 6 and 7 indicate coarse position of the point source 1, while variations in the phases of the fixed low and high frequencies indicate medium and fine position.

Since the point source is not located at a distance of infinity, the detected image pattern on the detector 5 is never equal to the dimensions of the image of the mask 3, but is always magnified with the magnification being as much as 1.05 to 1.10. The magnification factor $K_m$ is computed by taking the ratio of measured detector frequency to actual mask frequency preprogrammed into the computer.

The manner of measuring position in two dimensions in accordance with the teachings of the present invention will now be described in greater detail below.

In the preferred embodiment of the present invention, the mask is programmed with two series of waveforms that are related to one another as being located in two axes skewed with respect to each other and with respect to the axis of the detector 5. Each waveform preferably consists of a plurality of fixed low frequency waves followed by a plurality of variable frequency waves followed by a plurality of fixed high frequency waves. In the example of FIGS. 1–4 in which the detector 5 lies on the y axis (see, in particular, FIG. 4), one waveform is located along a line defined where y=z and the other waveform is located on a line defined as y=−z. These lines are orthogonal with respect to one another. The line defined by y=z may be described by the function g(y+z) and the line defined by y=−z may be described by the function h(y−z). The transmissivity equation is:

$$\text{Mask}(y,z) = g(y+z) + h(y-z) \quad (1)$$

Replacing g(y+z) and h(y−z) by their constituent functions, the mask transmissivity is described by:

$$\text{Mask}(y, z) = \quad (2)$$

$$0.5 + \frac{\left[\cos\left(F_{low1} \cdot \frac{(y+z)}{N} \cdot 2\pi\right) + \cos\left(F_{variable1} \cdot \frac{(y+z)}{N} \cdot 2\pi \cdot \left(1 + \frac{(y+z) - 2 \cdot N}{2 \cdot N} \cdot \text{mod}1\right)\right) + \cos\left(F_{high1} \cdot \frac{(y+z)}{N} \cdot 2\pi\right)\right]}{12} +$$

-continued $$\frac{\left[\cos\left(F_{low2} \cdot \frac{(y-z)}{N} \cdot 2\pi\right) + \cos\left(F_{variable2} \cdot \frac{(y-z)}{N} \cdot 2\pi \cdot \left(1 + \frac{(y-z) - 2 \cdot N}{2 \cdot N} \cdot \text{mod}2\right)\right) + \cos\left(F_{high2} \cdot \frac{(y-z)}{N} \cdot 2\pi\right)\right]}{12}$$

Where $F_{low1}$, $F_{low2}$, $F_{variable1}$, $F_{variable2}$, $F_{high1}$, $F_{high2}$, are low, variable and high frequency constituents, respectively, of the mask, and mod1, and mod2 are modulation factors. The detector lies on the y axis and has 1,024 elements or pixels, making N=1,024 in the equation.

FIGS. 5, 6 and 7 show FFTs for various pattern shifts with the middle two frequencies comprising variable transmissivity frequencies and being responsive in frequency to various image positions. The left two frequencies are fixed low frequencies and the right two frequencies are fixed high frequencies. These fixed frequencies are responsive in phase to various image positions.

Figure 8:
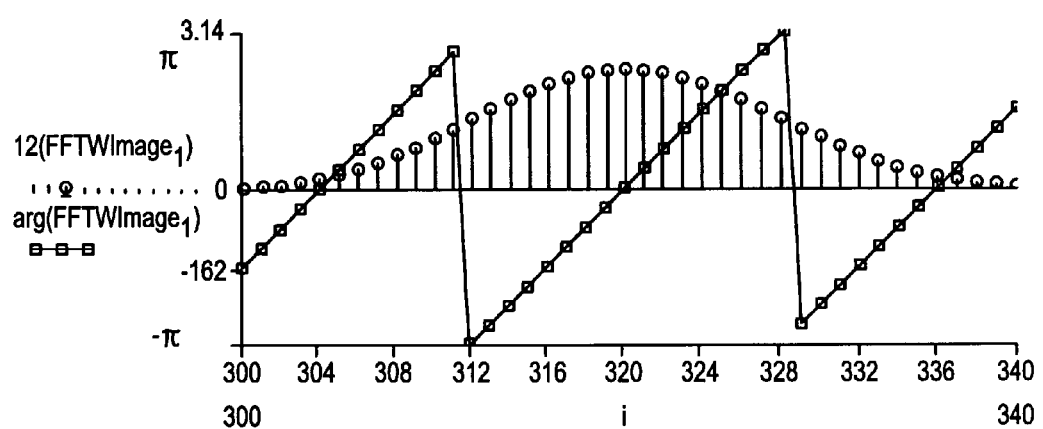
FIG. 8 shows a graph of a computed FFT showing both magnitude and phase.

From FFT plots, the spectral peaks are determined. The position in frequency of the variable frequencies indicates coarse position in each coordinate axis, while the phases of the fixed frequencies indicate medium and fine position in each coordinate axis. FIG. 8 shows the FFT magnitude and phase of a fixed frequency component.

Because the point source is not located at infinity, the detected image pattern is never equal to the mask image, but is always magnified, with magnifications as much as 1.05 to 1.10. The magnification ($K_m$) is computed by taking the ratio of the measured detector frequency to the actual mask frequency.

$$K_m = F\text{high1}_{mask}/F\text{high1}_{det} = F\text{high2}_{mask}/F\text{high2}_{det} \quad (3)$$

The following image shift calculation uses a mask with variable frequency ranging from Fmin to Fmax over a range of 3N pixels. The coarse pixel shift indicated by the variable frequency component is:

$$Y_{m\_var1} = [F\text{variable1}_{det} * K_m - F\text{mid1}_{mask}] / [F\text{max1}_{mask} - F\text{min1}_{mask}] * [3*N] \text{ pixels} \quad (4)$$

$$Y_{m\_var2} = [F\text{variable2}_{det} * K_m - F\text{mid2}_{mask}] / [F\text{max2}_{mask} - F\text{min2}_{mask}] * [3*N] \text{ pixels} \quad (5)$$

To compute the shift of the low and high frequency components, corresponding to medium and fine shifts, the phase at the array midpoint must be computed. The FFT routine returns the phase of frequencies at 0°, so to compute the midpoint phase, (i=511.5) the following expression is used:

$$\text{Arg}(F\text{low1}_{det})|_{i=511.5} = \text{Arg}(F\text{low1}_{det})|_{i=0} + \text{Mod}_{2\Pi}(511.5 * F\text{low1}_{det} * 2\Pi) \quad (6)$$

$$\text{Arg}(F\text{high1}_{det})|_{i=511.5} = \text{Arg}(F\text{high1}_{det})|_{i=0} + \text{Mod}_{2\Pi}(511.5 * F\text{high1}_{det} * 2\Pi) \quad (7)$$

$$\text{Arg}(F\text{low2}_{det})|_{i=511.5} = \text{Arg}(F\text{low2}_{det})|_{i=0} + \text{Mod}_{2\Pi}(511.5 * F\text{low2}_{det} * 2\Pi) \quad (8)$$

$$\text{Arg}(F\text{high2}_{det})|_{i=511.5} = \text{Arg}(F\text{high2}_{det})|_{i=0} + \text{Mod}_{2\Pi}(511.5 * F\text{high2}_{det} * 2\Pi) \quad (9)$$

The shifts relative to mask functions g(y+z) and h(y−z) are indicated by the fixed frequency components by:

$$Y_{m\_low1}=[P_{low1}+(Arg(Flow1_{det})|_{i=511.5}/2\Pi)]/Flow1_{mask} \quad (10)$$

$$Y_{m\_high1}=[P_{high1}+(Arg(Fhigh1_{det})|_{i=511.5}/2\Pi)]/Fhigh1_{mask} \quad (11)$$

$$Y_{m\_low2}=[P_{low2}+(Arg(Flow2_{det})|_{i=511.5}/2\Pi)]/Flow2_{mask} \quad (12)$$

$$Y_{m\_high2}=[P_{high}+(Arg(Fhigh2_{det})|_{i=511.5}/2\Pi)]/Fhigh2_{mask} \quad (13)$$

$$Z_{m\_high1}=Y_{m\_high1} \quad (14)$$

$$Z_{m\_high2}=-Y_{m\_high2} \quad (15)$$

Where $P_{low1}$ and $P_{low2}$ are determined from the variable frequency shift estimations $Y_{m\_var1}$ and $Y_{m\_var2}$, $P_{high1}$ and $P_{high2}$ are determined from the low frequency shift estimations $Y_{m\_low1}$ and $Y_{m\_low2}$.

$$P_{low1}=\text{Nearest\_Integer}[(Y_{m\_var1}*Flow1_{mask})-(Arg(Flow1_{det})|_{i=511.5}/2\Pi)] \quad (16)$$

$$P_{high2}=\text{Nearest\_Integer}[(Y_{m\_low2}*Fhigh2_{mask})-(Arg(Fhigh2_{det})|_{i=511.5}/2\Pi)] \quad (17)$$

The overall coordinates of incidence to the mask are computed by:

$$Y_m=Y_{m\_high1}+Y_{m\_high2} \quad (18)$$

$$Z_m=Z_{m\_high1}+Z_{m\_high2} \quad (19)$$

The angles of incidence to the mask are computed using:

$$\Theta_{ym}=\text{Tan}^{-1}(Y_m/X_m) \quad (20)$$

$$\Theta_{zm}=\text{Tan}^{-1}(Z_m/X_m) \quad (21)$$

Figure 9:
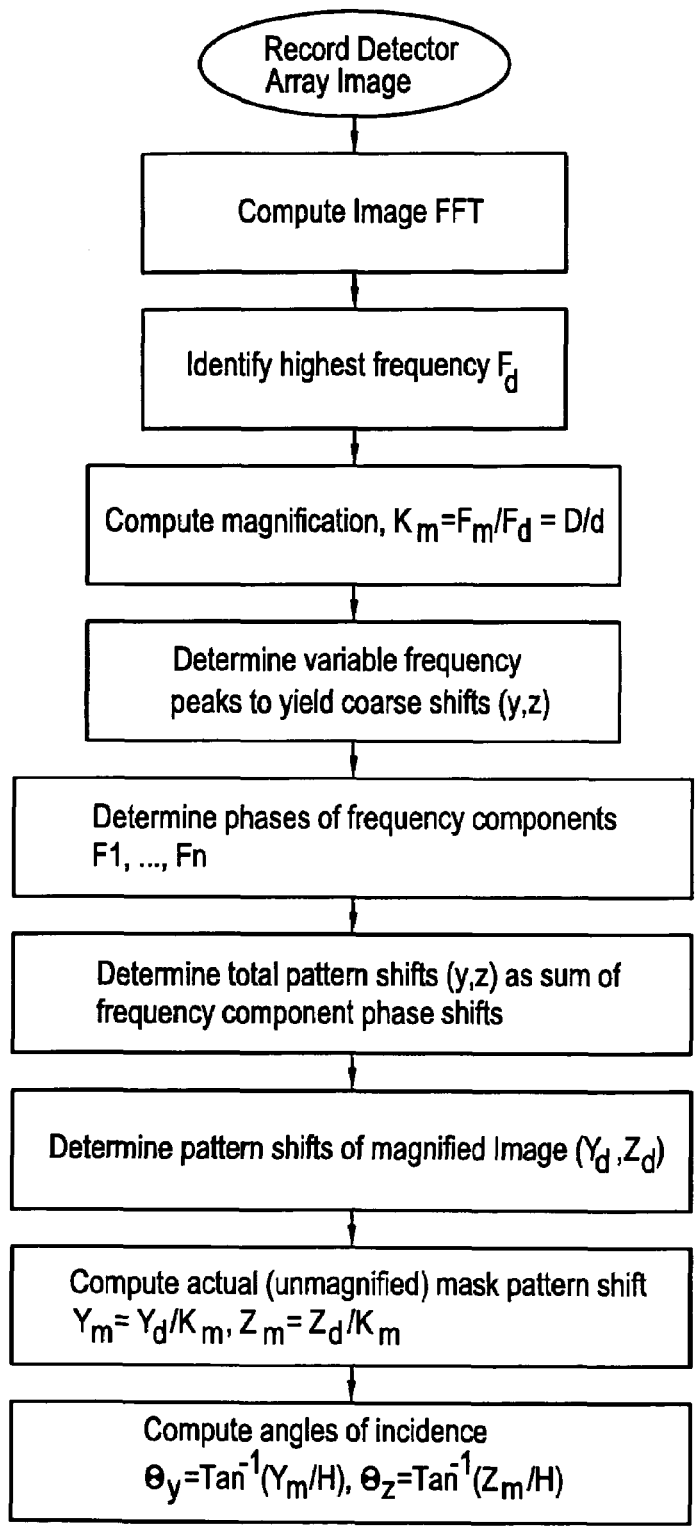
FIG. 9 shows a schematic representation of the method steps of the present invention.

FIG. 9 shows a block diagram of the calculation process.

As seen in FIG. 9, the first step in performing the method of the present invention is to record the detector array image and, therefrom, to compute the image Fast Fourier Transform (FFT). Next, the highest frequency $F_d$ is identified and then the magnification constant $K_m$ is computed.

Coarse measurements are then made by determining the peaks of the variable frequency waveforms $F_{variable}$ and, thereafter, the phases of the low and high frequency waveforms are determined. From those determinations, total pattern shifts as a sum of the frequency component phase shifts are determined and, therefrom, pattern shifts of the magnified image are calculated.

From these measurements and calculations, the actual unmagnified mask pattern shift is computed and, with this computation having been completed, the angles of incidence for the point source of light are accurately computed.

Figure 10:
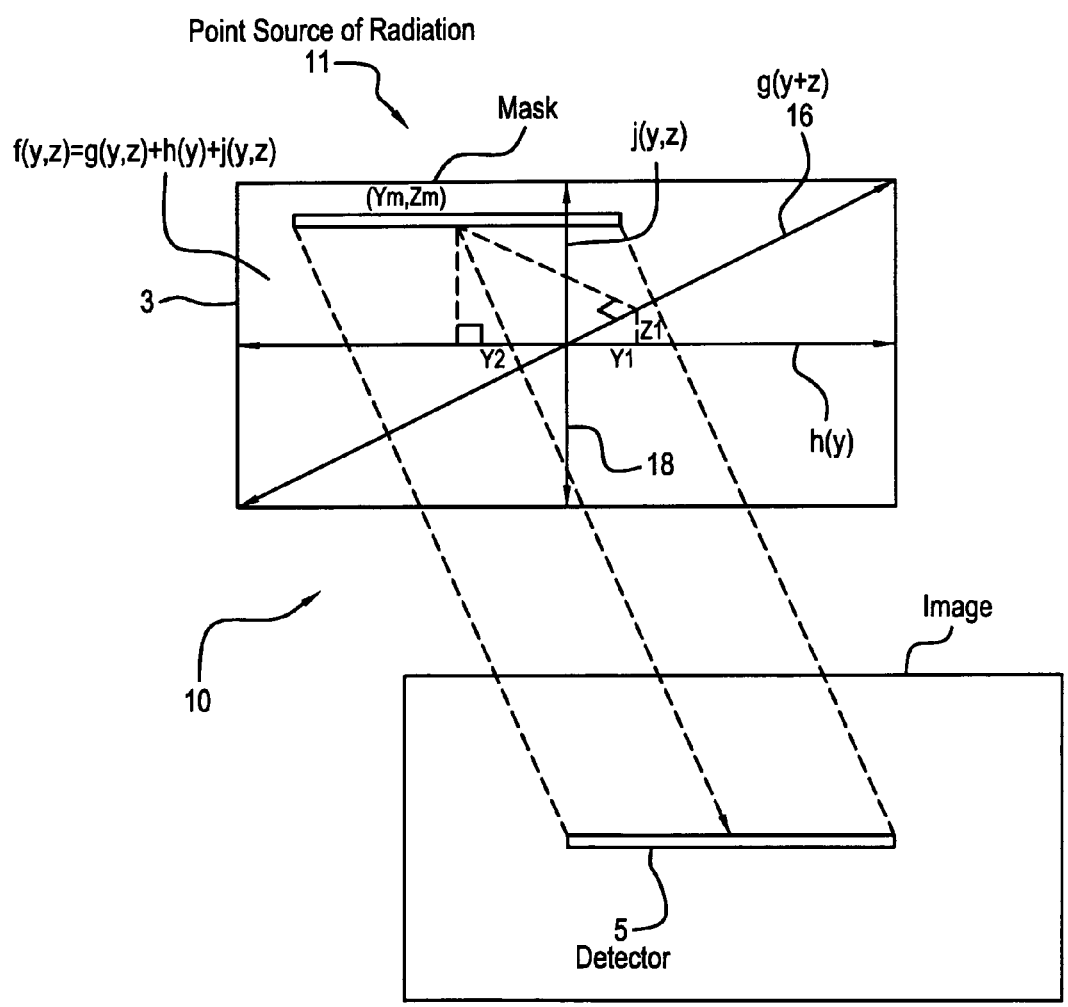
FIG. 10 shows a schematic representation of an alternative embodiment in which the mask pattern is placed in a configuration different from that of the embodiment best illustrated in FIG. 1.

A second embodiment of the present invention is schematically illustrated in FIG. 10. In FIG. 10, the system 10 is seen to include a point source of radiation 11, a mask 3, and a detector 5. The mask 3 has a pattern thereon including fixed low frequency, variable frequency, and fixed high frequency components oriented along the X axis and referred to in FIG. 10 by the function h(y). The mask 3 also has another pattern component oriented along the line Y=Z and referred to by the function g(y+z) which line is designated by the reference numeral 16 and is seen to extend diagonally across the mask 3. That component has fixed low and high frequency components. Additionally, a variable frequency component extends along the Z axis and is designated by the reference numeral 18 as well as by the function j(y,z). That component comprises a variable frequency component.

For this embodiment, the mask transmissivity function is:

$$\text{Mask}(y,z)=g(y+z)+h(y)+j(y,z) \quad (22)$$

Replacing g(y+z), h(y), and j(y,z) by their constituent functions, the mask transmissivity is described by:

$$\text{Mask}(y,z) = 0.5 + \frac{\left[\cos\left(F_{low1} \cdot \frac{y}{N} \cdot 2\pi\right) + \cos\left(F_{variable1} \cdot \frac{y}{N} \cdot 2\pi \cdot \left(1 + \frac{y-2 \cdot N}{2 \cdot N} \cdot \text{mod1}\right)\right) + \cos\left(F_{high1} \cdot \frac{y}{N} \cdot 2\pi\right)\right]}{12} + \frac{\left[\cos\left(F_{low2} \cdot \frac{(y+z)}{N} \cdot 2\pi\right) + \cos\left(F_{variable2} \cdot \frac{y}{N} \cdot 2\pi \cdot \left(1 + \frac{z-2 \cdot N}{2 \cdot N} \cdot \text{mod2}\right)\right) + \cos\left(F_{high2} \cdot \frac{(y+z)}{N} \cdot 2\pi\right)\right]}{12} \quad (23)$$

The calculations of image shift are:

$$Y_{m\_var1}=[Fvariable1_{det}*K_m-Fmid1_{mask}]/[F\max1_{mask}-F\min1_{mask}]*[3*N]\text{pixels} \quad (24)$$

$$Y_{m\_var2}=[Fvariable2_{det}*K_m-Fmid2_{mask}]/[F\max2_{mask}-F\min2_{mask}]*[3*N]\text{pixels} \quad (25)$$

To compute the shift of the low and high frequency components, corresponding to medium and fine shifts, and the function g(y+z), the phase at the array midpoint must be computed. The FFT routine returns the phase of frequencies at 0°, so to compute the midpoint phase, (i=511.5) the following expressions are used:

$$Arg(Flow1_{det})|_{i=511.5}=Arg(Flow1_{det})|_{i=0}+\text{Mod}_{2\Pi}(511.5*Flow1_{det}*2\Pi) \quad (26)$$

$$Arg(Fhigh1_{det})|_{i=511.5}=Arg(Fhigh1_{det})|_{i=0}+\text{Mod}_{2\Pi}(511.5*Fhigh1_{det}*2\Pi) \quad (27)$$

$$Arg(Flow2_{det})|_{i=511.5}=Arg(Flow2_{det})|_{i=0}+\text{Mod}_{2\Pi}(511.5*Flow2_{det}*2\Pi) \quad (28)$$

$$Arg(Fhigh2_{det})|_{i=511.5}=Arg(Fhigh2_{det})|_{i=0}+\text{Mod}_{2\Pi}(511.5*Fhigh2_{det}*2\Pi) \quad (29)$$

The shifts relative to mask functions g(y+z) and h(y−z) are indicated by the fixed frequency components by:

$$Y_{m\_low1}=[P_{low1}+(Arg(Flow1_{det})|_{i=511.5}/2\Pi)]/Flow1_{mask} \quad (30)$$

$$Y_{m\_high1}=[P_{high1}+(Arg(Fhigh1_{det})|_{i=511.5}/2\Pi)]/Fhigh1_{mask} \quad (31)$$

$$Y_{m\_low2}=[P_{low2}+(Arg(Flow2_{det})|_{i=511.5}/2\Pi)]/Flow2_{mask} \quad (32)$$

$$Y_{m\_high2}=[P_{high}+(Arg(Fhigh2_{det})|_{i=511.5}/2\Pi)]/Fhigh2_{mask} \quad (33)$$

$$Z_{m\_high1}=0 \quad (34)$$

$$Z_{m\_high2}=Y_{m\_high2} \quad (35)$$

Where $P_{low1}$ and $P_{low2}$ are determined from the variable frequency shift estimations $Y_{m\_var1}$ and $Y_{m\_var2}$, $P_{high1}$ and $P_{high2}$ are determined from the low frequency shift estimations $Y_{m\_low1}$ and $Y_{m\_low2}$, as follows:

$$P_{low1} = \text{Nearest\_Integer}[(Y_{m\_var1} * F\text{low1}_{mask}) - (Arg(F\text{low1}_{det})|_{i=511.5}/2\Pi)] \quad (36)$$

$$P_{high2} = \text{Nearest\_Integer}[(Y_{m\_low2} * F\text{high2}_{mask}) - (Arg(F\text{high2}_{det})|_{i=511.5}/2\Pi)] \quad (37)$$

The overall coordinates of incidence to the mask are computed by:

$$Y_m = Y_{m\_high1} \quad (38)$$

$$Z_m = Y_{m\_high2} + 2Y_{m\_high1} \quad (39)$$

The angles of incidence to the mask are computed using:

$$\Theta_{ym} = \text{Tan}^{-1}(Y_m/X_m) \quad (40)$$

$$\Theta_{zm} = \text{Tan}^{-1}(Z_m/X_m) \quad (41)$$

As such, an invention has been disclosed in terms of preferred embodiments thereof which fulfill each and every one of the objects of the invention as set forth hereinabove, and provide a new and useful sensor for determining the angular position of a radiating point source in two dimensions, of great novelty and utility, along with the method for determining the angular position.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A sensor for determining angular position of a radiating point source in two dimensions, comprising:
   a) a point source of light located in a prescribed space;
   b) a light detector adjacent said space;
   c) a two-dimensional mask interposed between said detector and said space, said mask having a two-dimensional surface pattern thereon formed by a prescribed pattern of frequencies and said surface pattern being entirely exposed to said space;
   d) whereby light from said source travels through said mask and onto said detector, said surface pattern causing at least one of phase or frequency changes to occur, said changes being used to calculate angular position of said point source of light with respect to said detector in two dimensions.

2. The sensor of claim 1, wherein said surface pattern includes at least one series of frequencies extending along a line consisting of at least one low frequency, at least one variable frequency, and at least one high frequency.

3. The sensor of claim 2, wherein said at least one series comprises a first series extending along a first line, and further including a second series extending along a second line and consisting of at least one low frequency, at least one variable frequency, and at least one high frequency.

4. The sensor of claim 3, wherein said first and second lines are orthogonal.

5. The sensor of claim 2, wherein said at least one series comprises a first series extending along a first line, and further including a second series extending along a second line.

6. The sensor of claim 5, wherein said second series consists of fixed low and high frequency components.

7. The sensor of claim 6, wherein a third series of frequencies is provided along a third line.

8. The sensor of claim 7, wherein said third series includes variable frequency components.

9. The sensor of claim 8, wherein said lines are non-parallel.

10. The sensor of claim 5, wherein said second series consists of variable frequency components.

11. The sensor of claim 10, wherein a third series of frequencies is provided along a third line.

12. The sensor of claim 11, wherein said lines are non-parallel.

13. The sensor of claim 2, wherein said at least one of phase or frequency changes comprises phase and frequency changes.

14. The sensor of claim 13, wherein said low and high frequencies exhibit phase variations.

15. The sensor of claim 13, wherein said variable frequency exhibits frequency variations on said detector.

16. The sensor of claim 15, wherein frequency variations are used to make coarse position measurements while phase variations are used to make medium and fine position measurements.

17. The sensor of claim 1, wherein said mask and detector lie in parallel planes.

18. The sensor of claim 1, wherein said at least one of phase or frequency changes comprises phase and frequency changes.

19. A sensor for determining angular position of a radiating point source in two dimensions, comprising:
   a) a point source of light located in a prescribed space;
   b) a light detector adjacent said space;
   c) a two-dimensional mask interposed between said detector and said space, said mask having a two-dimensional surface pattern thereon formed by a prescribed pattern of frequencies, said frequency pattern comprising first and second orthogonal lines, each of said lines having a series of frequencies thereon consisting of at least one low frequency, at least one variable frequency, and at least one high frequency;
   d) whereby light from said source travels through said mask and onto said detector, variations of frequency in said variable frequencies being used to calculate coarse position and variations in phase in said low and high frequency being used to calculate medium and fine position.

20. The sensor of claim 19, wherein said mask and detector lie in parallel planes.

* * * * *